United States Patent
Van De Rijdt et al.

(10) Patent No.: US 7,167,739 B2
(45) Date of Patent: Jan. 23, 2007

(54) ASSEMBLY OF MEDICAL EXAMINATION DEVICE AND A COMBINATION OF A FRAME AND A PATIENT TABLE AS WELL AS SUCH A COMBINATION

(75) Inventors: Johannes Hubertus Antonius Van De Rijdt, Eindhoven (NL); Johannes Julianus Marie Brouwers, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 21 days.

(21) Appl. No.: 10/493,800

(22) PCT Filed: Oct. 25, 2002

(86) PCT No.: PCT/IB02/04503

§ 371 (c)(1),
(2), (4) Date: Apr. 27, 2004

(87) PCT Pub. No.: WO03/037182

PCT Pub. Date: May 8, 2003

(65) Prior Publication Data

US 2004/0255382 A1 Dec. 23, 2004

(30) Foreign Application Priority Data

Oct. 29, 2001 (EP) .................... 01204130

(51) Int. Cl.
*A61B 6/04* (2006.01)
*A61G 13/02* (2006.01)
(52) U.S. Cl. .................... 600/415; 5/601; 378/209
(58) Field of Classification Search .............. 5/601, 5/600; 378/209; 600/415; 474/156, 157, 474/252, 253, 205, 206, 240, 245, 148, 212
See application file for complete search history.

(56) References Cited

U.S. PATENT DOCUMENTS

| | | | | | |
|---|---|---|---|---|---|
| 270,723 | A | * | 1/1883 | Aydelott | 474/212 |
| 379,784 | A | * | 3/1888 | Hill | 474/212 |
| 722,001 | A | * | 3/1903 | Dodge | 474/212 |
| 1,804,701 | A | * | 5/1931 | Mojonnier | 474/212 |
| 3,316,771 | A | * | 5/1967 | Nichols | 474/207 |
| 3,588,500 | A | * | 6/1971 | Koerner | 5/601 |
| 3,612,509 | A | * | 10/1971 | Boston et al. | 5/600 |
| 3,742,775 | A | * | 7/1973 | Hayes et al. | 474/140 |
| 3,744,095 | A | * | 7/1973 | Tomlinson | 474/205 |
| 4,254,666 | A | * | 3/1981 | Seredick | 474/253 |
| 4,552,347 | A | * | 11/1985 | Wallis | 5/601 |

(Continued)

FOREIGN PATENT DOCUMENTS

WO  WO 01/35828 A2 * 5/2001 .................. 378/209

*Primary Examiner*—Michael Safavi
(74) *Attorney, Agent, or Firm*—Thomas M. Lundin

(57) ABSTRACT

A medical examination device (1) comprising an examination space (3), a combination of a frame (5) and a patient table (4), and rack (8) which can be driven by a drive (9, 10) to displace a patient on the patient table into and out of the examination space. The rack comprises an elongated push-pull member (8) which is connected to the patient table and which has a length that exceeds the length of the patient table. As a result, the patient table can be displaced from the frame into the examination space over a distance that is larger than the length of the patient table.

12 Claims, 4 Drawing Sheets

U.S. PATENT DOCUMENTS

| | | | |
|---|---|---|---|
| 4,641,823 A * | 2/1987 | Bergman | 5/81.1 HS |
| 4,805,626 A * | 2/1989 | DiMassimo et al. | 600/415 |
| 4,979,929 A * | 12/1990 | Hynes | 474/206 |
| 4,990,124 A * | 2/1991 | Bartoletto et al. | 474/206 |
| 5,197,474 A * | 3/1993 | Englund et al. | 600/415 |
| 5,199,060 A * | 3/1993 | Kato | 378/196 |
| 5,199,123 A * | 4/1993 | Jacques et al. | 5/601 |
| 5,204,629 A * | 4/1993 | Ueyama | 600/415 |
| 5,210,893 A * | 5/1993 | Uosaki et al. | 5/601 |
| 5,272,776 A | 12/1993 | Kitamura | |
| 5,800,301 A * | 9/1998 | Anderson | 474/157 |
| 5,823,960 A * | 10/1998 | Young et al. | 600/415 |
| 6,424,854 B2 * | 7/2002 | Hayashi et al. | 600/415 |
| 6,473,918 B2 * | 11/2002 | Schaefer | 5/600 |
| 6,955,464 B1 * | 10/2005 | Tybinkowski et al. | 378/209 |
| 6,961,606 B2 * | 11/2005 | DeSilets et al. | 600/415 |
| 2004/0001571 A1 * | 1/2004 | Jahrling | 378/209 |

* cited by examiner

ASSEMBLY OF MEDICAL EXAMINATION DEVICE AND A COMBINATION OF A FRAME AND A PATIENT TABLE AS WELL AS SUCH A COMBINATION

BACKGROUND

The invention relates to an assembly of a medical examination device with an examination space and a combination of a frame and a patient table, said assembly further being provided with displacing means which are drivable by driving means and which are used to move a patient on the patient table into and out of the examination space, said displacing means comprising an elongated push-pull member that is connected to the patient table.

The invention also relates to a combination of a frame and a patient table for use in such an assembly.

An assembly of the type mentioned in the opening paragraph is known from U.S. Pat. No. 5,272,776. In said document a description is given of a shell-shaped MRI scanner. The examination space is situated in the interior of this shell shape. Persons to be examined are in a horizontal position on a patient table and are moved into the examination space. For this purpose, the patient table in the examination space is supported and guided by a number of rollers, while underneath an end portion of the patient table which always projects from the examination space there is provided a leg at the underside of which a swivel wheel is mounted that rests on the floor underneath on which the MRI scanner rests too. Substantially throughout its length, the patient table is provided with a toothed rack that is in mesh with a gear that is driven by a driving means that is incorporated within the wall thickness of the shell shape of the MRI scanner. In U.S. Pat. No. 5,272,776 additionally a number of alternative embodiments are described wherein use is made of a type of transmission other than a toothed rack transmission, such as a screwed-spindle transmission and a multiple linkage mechanism. All these embodiments have in common that the length of the patient table exceeds the length that is necessary to support a patient that is in a horizontal position. This can be attributed, on the one hand, to the fact that in the situation where the patient table is in the pulled-out state, said patient table necessarily still rests on at least the roller that, inside the examination space, is closest to the entrance side of the MRI scanner. As the patient positions himself, or is positioned, on the examination table outside the interior of the shell shape, it is inevitable, assuming that the patient is moved into the examination space head first, that a certain length of the patient table on the side of the head remains unused, at least for supporting the patient. In this sense, also on the foot side a certain length of the patient table remains unused, which can be attributed to the transmission chosen to push the patient table into and pull it out of the examination space. As a result, in the pushed-in state, a part of said patient table projects beyond the MRI scanner on the entrance side. This observation leads to the first important drawback of the known assembly, which is that the patient table is inherently longer than would be necessary for the height of a patient. A second important drawback resides in that the patient table and the MRI scanner form an inextricable combination as a result of which the patient must necessarily position himself on the patient table at the location of the MRI scanner, or if the patient is unable to do so, the patient is positioned on the patient table at said location by medical personnel.

SUMMARY

It is an object of the invention to provide an assembly of the type mentioned in the opening paragraph, wherein the above-mentioned drawbacks of the known assembly are precluded as much as possible.

To achieve this object, an assembly of the type mentioned in the opening paragraph is characterized in accordance with the invention in that the length of the elongated push-pull member exceeds the length of the patient table, enabling the patient table to be displaced between the frame and the examination space over a displacement distance that is larger than the length of the patient table.

By embodying the elongated push-pull member such that the length thereof exceeds the length of the patient table, which patient table may be shorter than the patient table of the above-described known assembly, it becomes possible to move the patient table over a distance that is larger than the length of the patient table, so that it could be said that it moves completely past itself, as it were.

To further limit the necessary length of the patient table, in accordance with a very advantageous embodiment, a frame for completely supporting the patient table is provided on the outside of the examination device. By using said frame it is no longer necessary for the patient table in the pulled-out state to be still partly within said examination space, or, in the case of a shell-shaped MRI scanner, to be within the interior of the shell shape.

It is very advantageous if the frame with the patient table can be removed from the examination device. This makes it possible for patients to position themselves, or to be positioned, on the patient table at a distance from the medical examination device, as a result of which the capacity utilization of the medical examination device can be increased. In addition, a removable frame including the associated patient table has the important advantage that a plurality thereof can be used simultaneously in combination with a single examination device. This means, for example, that while one patient lying on the patient table is being examined in the examination device, another patient on a second patient table including the associated frame can be collected and a third patient on a third patient table can be taken away.

If the driving means are rigidly attached to the frame, an independent unit of assembly and patient table is obtained that can be readily used in combination with different types of medical examination equipment, for example in combination with an MRI scanner as well as in combination with equipment for producing roentgenograms. An advantageous embodiment of such driving means is formed by an electric motor powered by an electric accumulator. Alternatively, it may also be advantageous to supply power to the driving means by connecting them to the mains supply. In this connection, it may further be observed that it is also necessary for the electronic control system of the assembly in accordance with the invention to communicate with the medical examination device as well as with the driving means for the necessary coordination.

In accordance with a very advantageous embodiment, the push-pull member is at least partly articulated. This enables said push-pull member to be housed within the length of the patient table in spite of the fact that the length of the push-pull member exceeds that of the patient table. As a result, no parts of the elongated push-pull member project beyond the patient table, which is very advantageous, in particular, when use is made of removable frames as described above.

A very advantageous embodiment of an at least partly articulated push-pull member is obtained if the push-pull member comprises rack elements which are pivotable with respect to each other about pivot pins, and which each comprise teeth, and the driving means comprise a gear for meshing with said teeth. The use of the pivot pins readily enables the push-pull member to extend in accordance with a curved trajectory, for example in accordance with a U-shaped trajectory. The geometry of the teeth can be optimized for the drive by the driving means. For example, use can be made of oblique teeth which provide a much quieter drive in combination with a larger power transmission. The use of the rack elements enables the patient table to be very accurately displaced in the examination space, which is very important, if one realizes that, for example in the case of an MRI scanner, it is often necessary to displace the patient table in the course of the examination to obtain an image of a (longitudinal) part of the body of the patient. In this connection an accurate displacement to obtain a correct coordination is very important, of course. In addition, the push-pull member comprising pivotable rack elements exhibits only a small sensitivity to wear precisely because the functions of pivoting and meshing for transmitting the drive are separate functions. This contrasts with a push-pull chain which is naturally characterized by comparatively large degrees of play and tolerances. In addition, an important advantage of the use of pivotable rack elements is formed by the fact that they can be manufactured in a comparatively simple manner.

Preferably, the pivot pins extend horizontally, so that a curvature of the elongated push-pull member can be initiated under the influence of gravity.

A very advantageous spacing between the pivot pins ranges between 0.05 m and 0.15 m. Such a spacing enables, on the one hand, a useful curvature of the push-pull member to be realized while, on the other hand, the number of pivot pins and the associated play remain limited.

A very advantageous embodiment of the assembly in accordance with the invention is characterized in that a first rack element comprises a stop serving as an abutment for a neighboring second rack element in order to lock the second rack element in an orientation that is in line with the first rack element. Such a locked situation is excellently suited for making the gear mesh with the driving means, whereby, in the case of a pushing load, at least buckling in one of the two possible buckling directions is precluded. Buckling in the other direction can be very suitably precluded by using a guide means along the trajectory of the push-pull member.

Preferably, the push-pull member forms a movable part of the frame. In this manner, it is precluded that the push-pull member would have to form part of the medical examination device, which would require special provisions at the location of the medical examination device, while the nature of said medical examination device is such that it is generally poorly suited for such provisions.

The invention further relates to a combination of a frame and a patient table for use in an assembly in accordance with the invention such as described hereinabove. It is important to observe that this combination can be embodied such that it can operate more or less autonomously in combination with different types of medical examination devices. It is also advantageous if a medical examination device is used in combination with a number of combinations of a frame and a patient table.

These and other aspects of the invention will be apparent from and elucidated with reference to the embodiment(s) described hereinafter.

BRIEF DESCRIPTIONS OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1A:
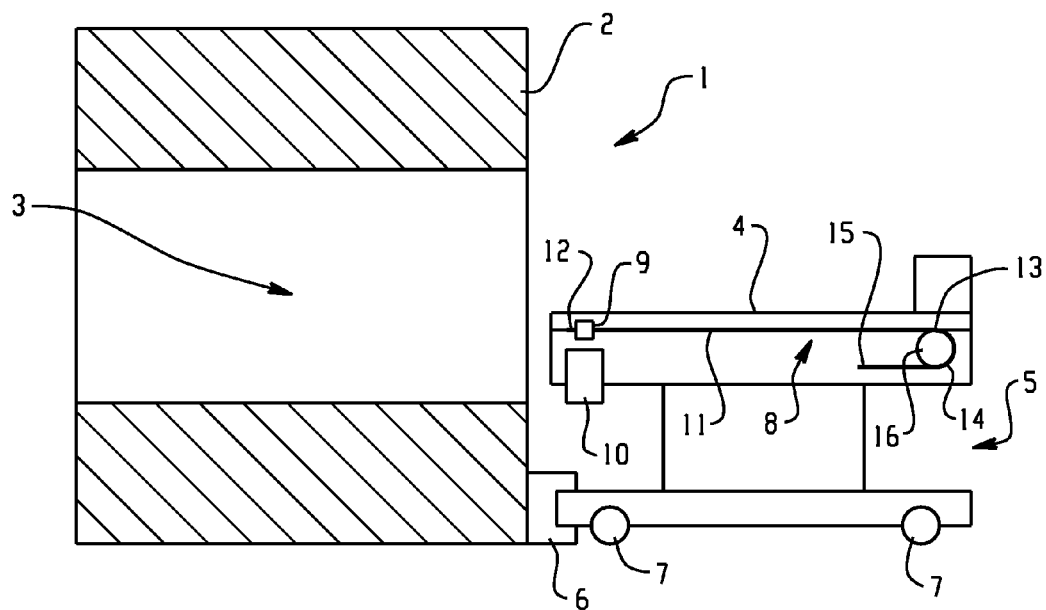
FIG. 1A shows a first assembly in accordance with the invention in the pulled-out state.
Figure 1B:
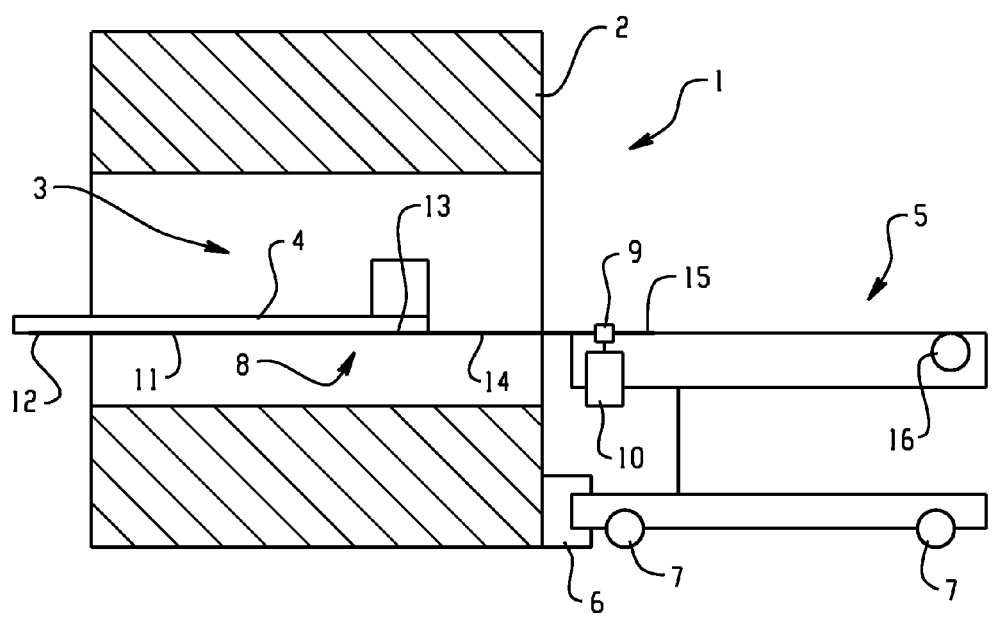
FIG. 1B shows the assembly in the pushed-in state.

FIGS. 1A and 1B show an MRI scanner which is substantially shell-shaped. Such MRI scanners are also referred to as closed MRI scanners. The body 2 of the shell shape accommodates all kinds of facilities, such as magnetic coils and cooling means. The interior of the shell shape forms an examination space 3 wherein the patient must be in order to be examined by the MRI scanner. For this purpose, a patient table 4 can be moved from a frame 5 (FIG. 1A) to the examination space 3 (FIG. 1B), and guiding means for the patient table 4, which are not shown in greater detail, are provided on the inner side of the body 2 of the shell. The frame 5 is unequivocally positioned relative to the MRI scanner 1 by means of a positioning element 6 that is rigidly connected to the MRI scanner 1, so that the patient table 4 can also be unequivocally moved into the examination space 3 where it is received by said guiding means. The frame 5 rests on wheels 7, so that, after the frame 5 has been disconnected from the positioning element 6, said frame with the patient table 4, on which a patient may or may not be present, can be displaced, for example to a hospital room.

A partly articulated toothed rack 8 is provided to enable the patient table 4 to be displaced, which toothed rack will be described in greater detail with reference to FIG. 2. In FIGS. 1A and 1B, the toothed rack 8 is denoted by means of a thick line. In the situation in accordance with FIG. 1A, the toothed rack 8 is substantially U-shaped, with the legs of the U-shape being unequal in length. To create this U-shape of the toothed rack 8, a pulley 16 is provided over which the toothed rack 8 is passed, if necessary guided by guiding means, during the movement from FIG. 1B to FIG. 1A. A gear 9 meshes with the toothed rack 8, which gear is driven by an electric motor 10. Said electric motor 10 is rigidly connected to the frame 5. The toothed rack 8 comprises a rigid, straight portion 11 extending between the end 12 and the transition point 13, and an articulated portion 14 extending from the transition point 13 to the end 15.

Figure 2:
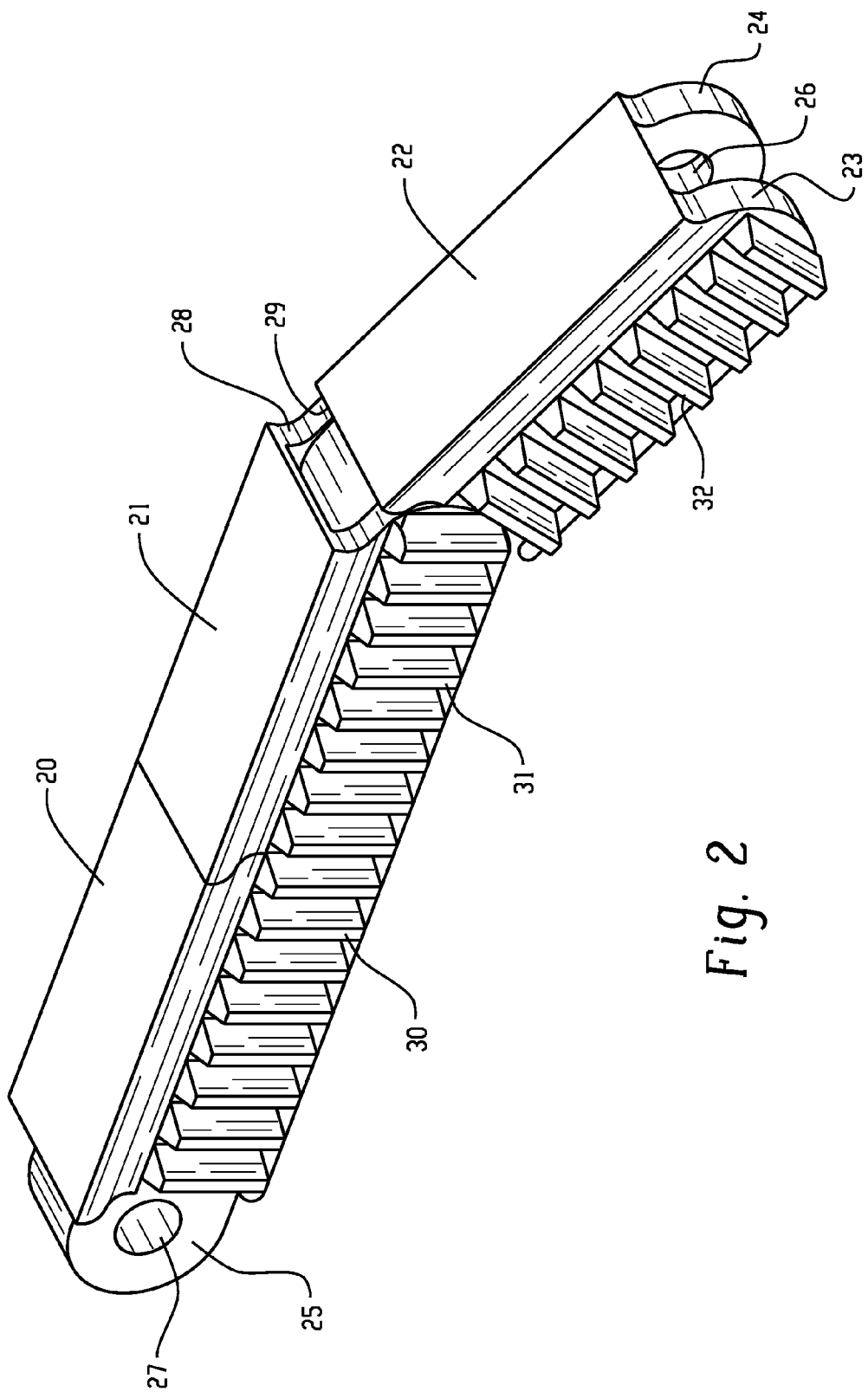
FIG. 2 shows three rack elements as used in the first assembly.

FIG. 2 shows three rack elements 20, 21, 22 that form part of the articulated portion 14 of rack 8. Rack elements 20, 21 are in line with each other, whereas rack element 22 includes an angle with the rack elements 20, 21. Such a situation arises during the transition from FIG. 1A to FIG. 1B. Each rack element 20, 21, 22 comprises, at one end, two spaced ears 23, 24 between which a nose 25 of a neighboring rack element can be positioned. The ears 23, 24 are provided with pin holes only one of which, i.e. pin hole 26, is shown in FIG. 2. Nose 25 is provided with a corresponding pin hole 27. If the nose 25 of a rack element is positioned between two ears 23, 24 of a neighboring rack element, the pin holes 26, 27 are coaxial, and a pivot pin, which is not shown in detail, can be inserted through the pin holes 26, 27 in ears 23, 24 and nose 25, as a result of which the two neighboring rack elements can pivot with respect to each other. The pivot pins are horizontally oriented, so that the rack element 22 can pivot in a downward direction under the influence of gravity, in which case, for example, rack elements 20, 21 are supported, unlike rack element 22, by a guiding means. The center-to-center distance between the different rack elements is 0.10 m. Each rack element 20, 21, 22 is provided, above the ears 23, 24, with a stop edge 28 serving as an abutment for an edge 29 of a neighboring rack element which is situated opposite said stop edge 28. The cooperation between stop edge 28 and edge 29 of neighboring rack elements ensures that the pivotal motion of a rack element from the situation where the rack elements are in line with each other can only take place in one direction. This is important, in particular, in the case of a pushing load that might lead to symptoms of buckling. Stop edge 28 and edge 29 now at least preclude buckling in one direction, while buckling in the opposite direction can be precluded, for example, by using a guiding means for the rack elements. In the perspective view shown in FIG. 2, each rack element is provided at the front side with a row of teeth 30, 31, 32. If the rack elements 20, 21, 22 are in line with each other, the teeth 30, 31, 32 form a regular pattern similar to one long conventional rack. Although, in FIG. 2, the teeth 30, 31, 32 are situated on the front side, they may alternatively be provided on the rear side, lower side or upper side. Of course, this does require an adaptation of the position and orientation of gear 9. The provision of the teeth 30, 31, 32 on the upper side has the advantage that, in the case of a pushing load, edges 29 and stop edges 28 are properly pressed together, so that buckling can be precluded. Teeth on the upper side can also be combined with teeth on the lower side, for which latter teeth a separate gear is provided. A pushing load causes the upper row of teeth to be used, whereas a tensile load causes the lower row of teeth to be used.

Figure 3:
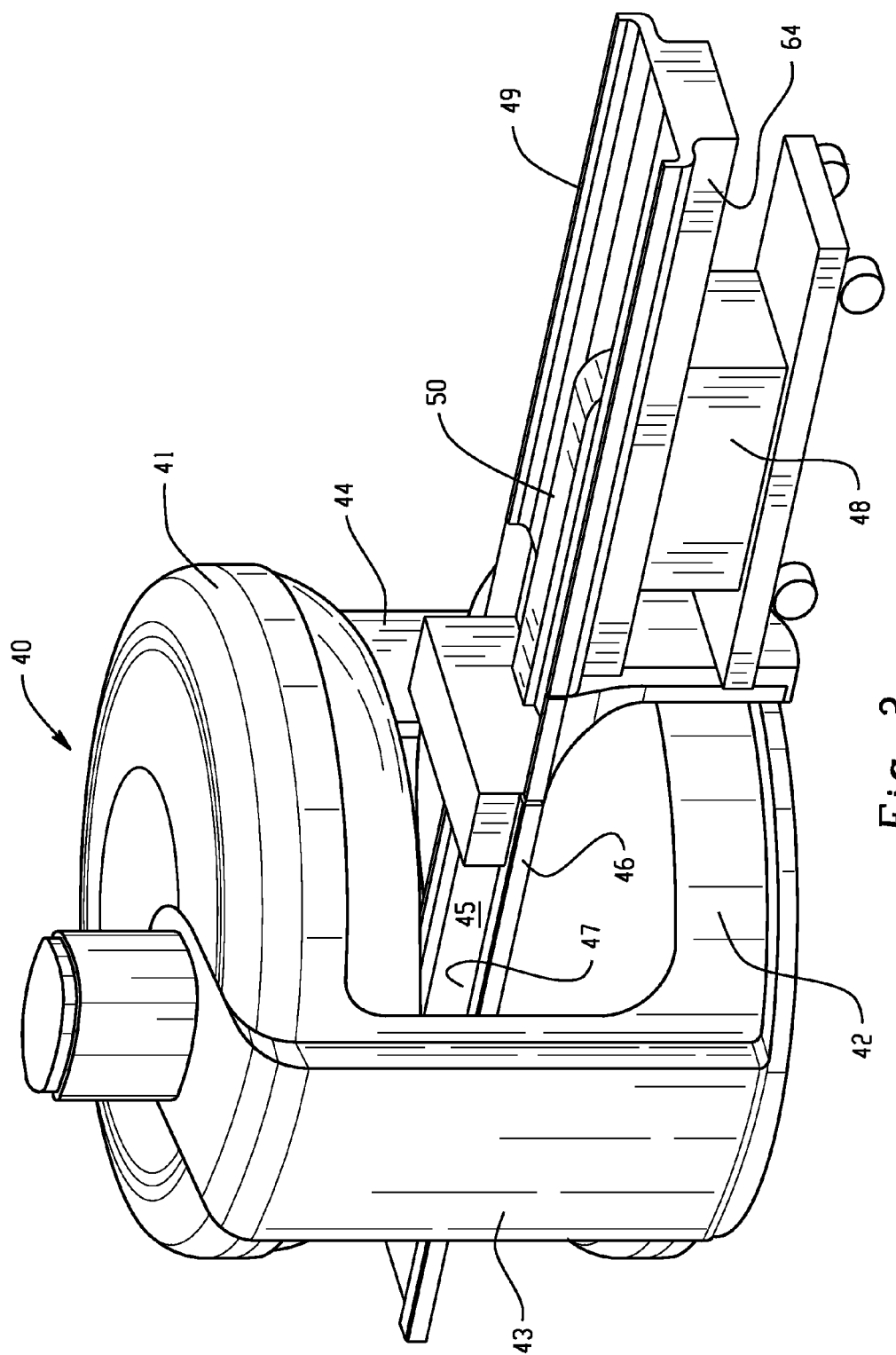
FIG. 3 shows a second assembly in accordance with the invention in the pushed-in state.

FIG. 3 shows an open-type MRI scanner 40. Said MRI scanner 40 is substantially built up of two disc-shaped housings 41, 42 accommodating ring-shaped coils, not shown in detail, for generating a magnetic field. Said two disc-shaped housings 41, 42 are interconnected by means of two vertical connecting arms 43, 44. Between the disc-shaped housings 41, 42 and the vertical connecting arms 43, 44 there is an examination space 45. Inside said examination space 45, the MRI scanner 40 is provided with a guiding means 46 for a patient table 47. In the situation shown in FIG. 3, the patient table 47 is in the pushed-in state, i.e. the patient table is inside the examination space 45. Next to the MRI scanner 40 there is a mobile frame 48 that is also provided with a guiding system 49 for the patient table 47. To displace the patient table 47 between a pushed-in state and a pulled-out state, the frame 48 is provided with a rack 50 that is connected with the patient table 47, at the lower side thereof, substantially throughout the length of said patient table 47. This part of the rack 50 is rigidly constructed. The part of the rack 50 extending beyond the patient table 47 is flexibly constructed.

Figure 4:
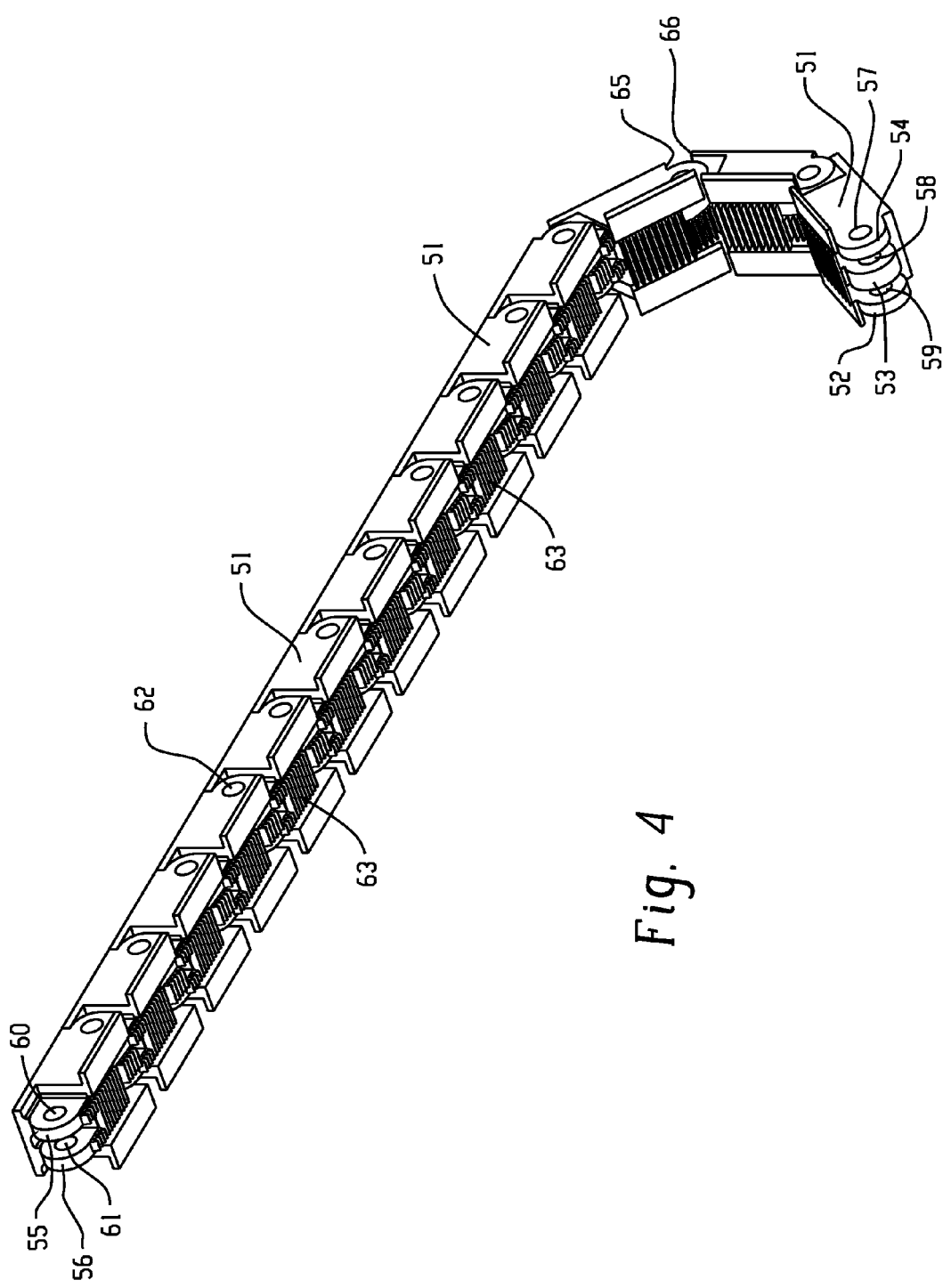
FIG. 4 shows a number of rack elements such as used in the second assembly.

The flexible part of the rack 50 is shown in FIG. 4 in a perspective bottom view. This flexible part of rack 50 comprises a number of rack elements 51 which are pivotable with respect to each other. The rack elements 51 are each provided, at one end, with three ears 52, 53, 54 between which noses 55, 56 can be accommodated, so that bores 57, 58, 59 in the ears 52, 53, 54 and bores 60, 61 in noses 55, 56 extend coaxially for receiving a pivot pin 62. Over the width of the two noses 55, 56, between which the middle ear 53 is sandwiched, the rack elements 51 are provided with teeth 63 in such a manner that, if the rack elements 51 are in the stretched state, the teeth 63 jointly exhibit a regular pattern for meshing with a gear that is not shown. This gear forms part of the frame 48 and is situated within protection 64, on the side of the frame 48 which faces the MRI scanner, in a longitudinal position similar to that of gear 9 in FIGS. 1A and 1B. The gear can be rotatably driven by driving means that also form part of the frame 48. Unlike the situation shown in FIGS. 1A, 1B and 2, the axis of rotation for the gear is horizontally oriented, i.e. perpendicularly to the longitudinal direction of the rack 50. To mesh with the teeth of rack 50, which teeth are formed partly by the teeth 63 of the flexible part of the rack 50, said gear is situated below the rack 50.

On the side facing away from the teeth 63, the rack elements 51 are provided, on the one hand, with a stop edge 65 and, on the other hand, with an edge 66 for butting against the stop edge 65. The presence of stop edges 65 and edges 66 ensures that the mutual pivotal motion of rack elements 51 from the stretched state can take place in one direction only.

The configuration of the rack 50 as shown in FIG. 4 has the advantage that, in comparison with the rack 8 shown in FIG. 2, said rack 50 can be constructed so as to be flatter and hence takes up less space in the vertical direction within the examination space 45. In this respect, it is important to realize that an increase of the distance between the two disc-shaped housings 41, 42 causes the cost price of the MRI scanner 40 to rise, but of course the space, or at least the vertical distance, that must be available for a patient is a limiting condition.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An assembly of a medical examination device with an examination space and a combination of a frame and a patient table, said assembly further being provided with displacing means which are drivable by driving means and which are used to move a patient on the patient table into and out of the examination space, said displacing means including:

an elongated, articulated push-pull member that is attached to the patient table, the drive member including a plurality of rack members connected by pins, which rack members are disposed linearly, end-to-end when the patient table is extended and are disposed at least partially articulated when the table is retracted, a first rack element comprises a stop serving as an abutment for a neighboring second rack element in order to lock the second rack element in an orientation that is in line with the first rack element, as the patient table is extended.

2. An assembly as claimed in claim 1, wherein the frame with the patient table can be removed from the examination device.

3. An assembly as claimed in claim 1, wherein the driving means are rigidly attached to the frame.

4. An assembly as claimed in claim 1, wherein the push-pull member is a movable part of the frame.

5. A combination of a frame and a patient table for use in an assembly as claimed in claim 1.

6. A patient support assembly for supporting a patient in a diagnostic imaging apparatus, the assembly comprising:
a frame disposed adjacent the diagnostic imaging apparatus;
a patient table guide means mounted to the imaging apparatus;
a patient table mounted for movement along the frame and the guide means to move the patient table into and out of a diagnostic imaging space;
an at least partially articulated push-pull member having one end affixed to the patient table and a second end slidingly received in the frame for pushing and pulling the patient table along the frame and the guide means, the push-pull member being articulated to be fully received in the frame when the patient table is supported only by the frame and only partially received in the frame when the patient table is fully extended, a length of the push-pull member exceeding a length of the frame such that the push-pull member can push the patient table to a position displaced from the frame supported on the guide means and pull the table to a position supported on the frame.

7. An assembly as claimed in claim 6, wherein
the push-pull member comprises rack elements which are pivotable relative to each other about pivot pins and which each include teeth, and
the driving means comprise a gear for meshing with said teeth.

8. An assembly as claimed in claim 7, wherein the pivot pins extend horizontally.

9. An assembly as claimed in claim 7, wherein the spacing between the pivot pins ranges between 0.05 meter and 0.15 meter.

10. A patient support assembly for moving a patient into and out of an examination region of a diagnostic imaging apparatus which includes a table guide, the assembly comprising:
a frame disposed adjacent the diagnostic imaging apparatus;
a patient table mounted for movement along the frame and the table guide such that the patient table is movable into and out of the examination region;
a drive for driving the patient table into and out of the diagnostic imaging region, the drive assembly including:
a plurality of partially articulated rack elements, a leading end rack element being affixed to the patient table for movement therewith, the rack elements assuming an end-to-end linear relationship behind the leading end rack element to define a non-flexing linear assembly for pushing the patient table along the table guide,
the plurality of rack elements extended in the linear orientation to have a linear length longer than the frame to extend beyond the frame for pushing the patient table along the table guide of the diagnostic imaging apparatus displaced from the frame,
pivot elements pivotally connecting the rack elements which permit the rack elements to articulate and fold as the patient table is retracted such that the plurality of rack elements fit fully into the frame when the patient table is in a fully retracted position supported only by the frame, and
a motor drive which engages and drives the linearly oriented rack members to push the patient table along the table guide into the imaging region of the diagnostic imaging apparatus and to pull the patient table out of the examination region onto the frame, the rack members articulating downstream from the motor assembly.

11. The assembly as claimed in claim 10, wherein the rack members include stop arrangements which block the rack elements from articulating in the linear orientation when pushing the patient table and which permit rack elements to pivot out of the linear arrangement in only a single direction as the table is retracted.

12. The assembly as claimed in claim 11, wherein the stop arrangement permit the rack elements to pivot only downward away from the patient table.

* * * * *